(12) United States Patent
Filippini et al.

(10) Patent No.: US 8,637,058 B2
(45) Date of Patent: Jan. 28, 2014

(54) COMPOSITIONS BASED ON CUPRIC SALTS, CUPRIC SALTS AND THEIR USE FOR CONTROLLING PHYTOPATHOGENS

(75) Inventors: Lucio Filippini, Milan (IT); Marilena Gusmeroli, Monza-Milan (IT); Alexia Elmini, Buronzo-Vercelli (IT); Carlo Garavaglia, Cuggiono-Milan (IT); Luigi Mirenna, Milan (IT)

(73) Assignee: Isagro S.p.A., Milan (IT)

( * ) Notice: Subject to any disclaimer, the term of this patent is extended or adjusted under 35 U.S.C. 154(b) by 2459 days.

(21) Appl. No.: 10/494,610

(22) PCT Filed: Nov. 18, 2002

(86) PCT No.: PCT/EP02/12982
§ 371 (c)(1),
(2), (4) Date: Mar. 14, 2005

(87) PCT Pub. No.: WO03/043971
PCT Pub. Date: May 30, 2003

(65) Prior Publication Data
US 2005/0256091 A1    Nov. 17, 2005

(30) Foreign Application Priority Data
Nov. 19, 2001 (IT) .................................. MI01A2430

(51) Int. Cl.
| | |
|---|---|
| A01N 25/00 | (2006.01) |
| A01N 59/20 | (2006.01) |
| A01N 37/36 | (2006.01) |
| A01N 43/54 | (2006.01) |
| A01N 43/40 | (2006.01) |
| A01N 43/78 | (2006.01) |
| A01N 43/64 | (2006.01) |
| A01N 43/50 | (2006.01) |
| A01N 43/38 | (2006.01) |
| A01N 43/32 | (2006.01) |
| A01N 47/10 | (2006.01) |
| A01N 47/28 | (2006.01) |
| A01N 47/40 | (2006.01) |
| A01N 55/02 | (2006.01) |
| A01N 37/12 | (2006.01) |
| A01N 37/44 | (2006.01) |
| A01N 33/02 | (2006.01) |
| A01N 33/24 | (2006.01) |
| A01N 33/18 | (2006.01) |
| A61K 31/535 | (2006.01) |

(52) U.S. Cl.
USPC .......... 424/405; 424/632; 424/633; 424/638; 514/136; 514/239.5; 514/269; 514/317; 514/370; 514/383; 514/398; 514/418; 514/434; 514/479; 514/482; 514/494; 514/538; 514/539; 514/649; 514/655; 514/741

(58) Field of Classification Search
USPC .................. 424/405, 632, 633, 638; 514/163, 514/239.5, 269, 317, 370, 383, 398, 418, 514/434, 479, 482, 494, 538, 439, 649, 655, 514/741
See application file for complete search history.

(56) References Cited

U.S. PATENT DOCUMENTS 3,995,034 A * 11/1976 Strobel .......................... 514/159
5,470,876 A * 11/1995 Proctor .......................... 514/492
5,756,524 A    5/1998 Riordan et al.
(Continued)

FOREIGN PATENT DOCUMENTS

DE        299 034       3/1992
EP        0 453 922     10/1991
(Continued)

OTHER PUBLICATIONS

Fred J. Meyer and Ralph M. Gooch, "Copper 3-Phenylsalicylate New Preservative for Special Applications to Wood", Industrial and Engineering Chemistry, 1952, 44(7), 1586-1589.*

(Continued)

Primary Examiner — Sue Liu
Assistant Examiner — Nathan W Schlientz
(74) Attorney, Agent, or Firm — Hedman & Costigan, P.C.; James V. Costigan; Kathleen A. Costigan

(57) ABSTRACT

Composition for controlling phytopathogens comprising compound of the formula:

$$\left[ (R_2)_n \underset{}{\underset{}{\bigcirc}} \overset{X-R_1}{\underset{C(=O)O}{}} \right]_2 Cu \quad (I)$$

wherein:
R$_1$ represents H, or a CO—R' acyl group;
R$_2$, the same or different when n is equal to 2, is a halogen, optionally selected from fluorine, chlorine, bromine or iodine; a C$_1$-C$_9$ alkyl group; a C$_1$-C$_9$ haloalkyl group; a C$_1$-C$_9$ alkoxyl group; a C$_1$-C$_9$ haloalkoxyl group; a C$_1$-C$_9$ thioalkyl group; a C$_1$-C$_9$ halothioalkyl group; a C$_3$-C$_9$ cycloalkyl group; a C$_2$-C$_{10}$ carboalkoxyl group; a cyano group; a hydroxyl group;
R' represents a hydrogen; a C$_1$-C$_9$ alkyl group; a C$_1$-C$_9$ haloalkyl group; a C$_1$-C$_9$ alkoxyl group; a C$_1$-C$_9$ haloalkoxyl group; a C$_2$-C$_{10}$ carboalkoxyl group; a phenyl group;
n is a number ranging from 0 to 2;
X represents an oxygen atom, a nitrogen or sulfur atom in combination with a fungicide; method for controlling phytopathogens with compound of formula (1) with or without another fungicide.

16 Claims, No Drawings

(56) References Cited

U.S. PATENT DOCUMENTS

| | | | | |
|---|---|---|---|---|
| 6,096,769 | A | * | 8/2000 | Perlitz et al. ............... 514/361 |
| 6,294,186 | B1 | * | 9/2001 | Beerse et al. ............... 424/405 |
| 6,503,936 | B1 | * | 1/2003 | Schelberger et al. ......... 514/383 |

FOREIGN PATENT DOCUMENTS

| | | | |
|---|---|---|---|
| FR | 2 140 269 | | 1/1973 |
| WO | WO 97/15189 | | 5/1997 |
| WO | WO 00/30450 | * | 6/2000 |
| WO | WO 02/39963 | | 5/2002 |

OTHER PUBLICATIONS

Chemical Abstracts Service, Columbus, Ohio, US JHA, Raj Ranjan, et al: "Structure and derivatographic strudy of 3-d series transition metal compleses with salicylic acid".

Chemical Abstracts Service, Columbus, Ohio, US Lucanska, B. et al: anti-inflammatory activity of aqua (dihydroxybenzoato) copper II complexes.

Chemical Abstract Service, Columbus Ohio, US Micera, G. et al : Interaction of metal-ions with humic-like models.

Chemical Abstracts Service, Columbus, Ohio, US, Sokolik, Jozef, et al: Anti-inflammatory activity of aqua (dihydroxybenzoato) copper II complexes.

Chemical Abstract Service, Columbus Ohio, US Cariati, F. et al: Interaction of metal-ions with humic-like models.

Chemical Abstract Service, Columbus Ohio, US Hulkova O. et al: EPR and electronic spectra of cresotatoaquocopper (II) complexes.

Chemical Abstract Service, Columbus Ohio, US Melink, Milan et al: Crystal structure spectral and magnetic behavior of copper (II) (5-chlor-osalicylato)2(aqua)2.

Chemical Abstracts Service, Columbus, Ohio, US, Sokolik, Jozef, et al: anti-inflammatory and antipyretic activities of the aqua (dihydroxybenzoato) copper II complexes.

Derwent Publicatins Ltd. Columbus Ohio, US Sokolik, Josef et al: suppressing growth of sulphate-reducing bacteria in oil deposits—by injecting water contg . . . salt.

Chemical Abstract Service, Columbus, Ohio, US Liu,Ziru, et al Thermal decomposition of cupric benzoates with two substituents.

Chemical Abstract Service, Columbus Ohio US. Verrall, A.F. et al Discloses preservative treatments for protecting wood boxes.

\* cited by examiner

COMPOSITIONS BASED ON CUPRIC SALTS, CUPRIC SALTS AND THEIR USE FOR CONTROLLING PHYTOPATHOGENS

The present invention relates to compositions based on cupric salts for controlling phytopathogens.

The present invention also relates to cupric salts of derivatives of salicylic acid and their application for the control of phytopathogens.

Salicylic acid is a compound naturally present in many vegetables. It is definitely present in extracts of willow bark, used since antiquity as an anti-inflammatory remedy.

Nowadays, salicylic acid is conveniently synthesized on an industrial scale by the condensation of a phenolic salt with carbon dioxide. Many of its derivatives can be easily prepared by exploiting the particular reactivities of the phenolic ring, of the carboxylic group and phenolic hydroxyl. In particular, acetylsalicylic acid is universally known as a pharmaceutical product.

It has been demonstrated that salicylic acid is capable of controlling various phytopathogens through the precocious induction of defense systems naturally present in plants, but activated after infection. The presence of phytopathogens, in fact, causes a series of biochemical signals, among which an accumulation of salicylic acid in the vegetable tissues, which lead, for example, to the synthesis of specific proteins with a fungicidal activity.

It has been shown that an increase in the level of salicylic acid induced previous to fungal infections, causes a much more effective fungicidal response on the part of the plant itself (THE PLANT CELL, Vol. 8 (1996) pages 1809-1819).

To enable a fungicide to be economically acceptable in agronomic practice, it is essential for it to ensure a reliable and prolonged fungicidal action. The use of salicylic acid as such has been described as providing lower protective levels than those of other classical fungicides. For example, it is said that the control of grape mildew by the use of salicylic acid as such, is much lower than that obtained by the use of traditional cupric products.

The applicant has now found that cupric salts of some derivatives of salicylic acid are particularly convenient, with respect to those described in the state of the art, for controlling bacterial and fungal phytopathogens. The applicant has found, in fact, that cupric salts of some derivatives of salicylic acid, when appropriately formulated, allow a prolonged protective action to be obtained on vegetables subjected to treatment, comparable to that of full doses of traditional cupric salts.

The cupric salts of derivatives of salicylic acid, object of the present invention, are moreover more effective than the corresponding non-salified derivative of salicylic acid, or salified with a different metal, in controlling phytopathogens on vegetables or parts thereof. This activity can be attributed to a concomitant induction effect reinforced by the direct action of the cupric ion. The activity registered is, in fact, also higher than that produced using a derivative of non-salified salicylic acid mixed with a traditional cupric fungicide.

An important aspect of the use of salts, object of the present invention, derives from the fact that the defense systems of plants activated by derivatives of salicylic acid have different action mechanisms and consequently allow an immunizing response which minimizes any possible production of resistant strains.

The applicant has also found that these salts form an excellent means of controlling phytopathogens also in vegetable varieties genetically modified for amplifying the original natural defense systems or in which one or more genes have been inserted, expressing fungicidal proteins as a result of variations in the content of salicylic acid itself in the tissues.

The applicant has additionally found that the joint application of salts of derivatives of salicylic acid, object of the present invention, with other active principles gives rise to a positive synergy of biological effects, which enable an excellent control of phytopathogens even resistant to said active principles, also on vegetables which have been genetically modified.

The present invention therefore relates to the use of cupric salts of derivatives of salicylic acid mixed with other active principles for the control of phytopathogens. Furthermore, the present invention also relates to some cupric salts of derivatives of salicylic acid as such and their use for the control of phytopathogens and the cupric salts themselves.

An object of the present invention consequently relates to fungicidal compositions containing one or more salts of derivatives of salicylic acid having formula (I):

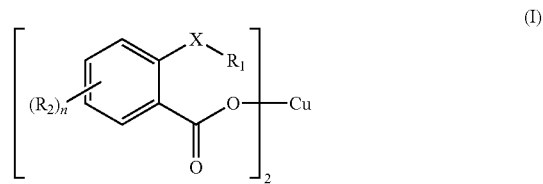

wherein:
$R_1$ represents H, or a CO—R' acyl group;
$R_2$, the same or different when n is equal to 2, is a hydrogen, a halogen, optionally selected from fluorine, chlorine, bromine or iodine; a $C_1$-$C_9$ alkyl group; a $C_1$-$C_9$ haloalkyl group; a $C_1$-$C_9$ alkoxyl group; a $C_1$-$C_9$ haloalkoxyl group; a $C_1$-$C_9$ thioalkyl group; a $C_1$-$C_9$ halothioalkyl group; a $C_3$-$C_9$ cycloalkyl group; a $C_2$-$C_{10}$ carboalkoxyl group; a cyano group; a phenyl group; a hydroxyl group;
R' represents a hydrogen; a $C_1$-$C_9$ alkyl group; a $C_1$-$C_9$ haloalkyl group; a $C_1$-$C_9$ alkoxyl group; a $C_1$-$C_9$ haloalkoxyl group; a $C_2$-$C_{10}$ carboalkoxyl group; a phenyl group;
n is a number ranging from 0 to 2;
X represents an oxygen atom, a nitrogen or a sulfur atom; in any molar ratio, with at least one fungicidal compound not corresponding to a salt of derivatives of salicylic acid having formula (I).

The compounds having formula (I) can also be present in a hydrated form by the coordination of any number of water molecules.

A further object of the present invention relates to salts of derivatives of salicylic acid having formula (I):

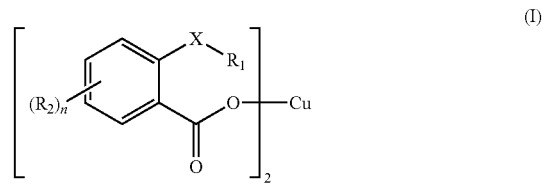

wherein:
$R_1$ represents H, or a CO—R' acyl group;
$R_2$, the same or different when n is equal to 2, is a halogen, optionally selected from fluorine, chlorine, bromine or iodine; a $C_1$-$C_9$ alkyl group; a $C_9$-$C_9$ haloalkyl group; a $C_1$-$C_9$ alkoxyl group; a $C_1$-$C_9$ haloalkoxyl group; a $C_1$-$C_9$ thioalkyl group; a $C_1$-$C_9$ halothioalkyl group; a $C_3$-$C_9$ cycloalkyl group; a $C_2$-$C_{10}$ carboalkoxyl group; a cyano group; a phenyl group; a hydroxyl group;
R' represents an alkyl group, optionally selected from methyl, propyl, isopropyl; or the haloalkyl group trifluoromethyl; or hydrogen;
n is a number ranging from 0 to 2;

X represents an oxygen atom, a nitrogen or a sulfur atom; with the exception, when X is equal to oxygen, of compounds wherein $R_1$ represents the acyl group $COCH_3$ and $R_2$ is hydrogen or chlorine and compounds wherein $R_1$ represents the acyl group COiPr or COEt and $R_2$ is hydrogen.

The compounds having formula (I) can also be present in hydrated form by the coordination of any number of water molecules.

A further object of the present invention relates to the use of derivatives of salicylic acid having formula (I):

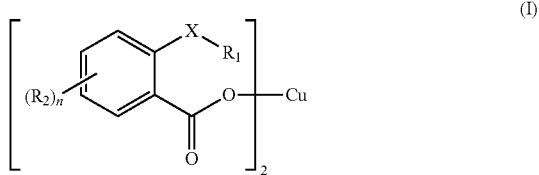

wherein:
$R_1$ represents H, or a CO—R' acyl group;
$R_2$, the same or different when n is equal to 2, is a halogen, optionally selected from fluorine, chlorine, bromine or iodine; a $C_1$-$C_9$ alkyl group; a $C_1$-$C_9$ haloalkyl group; a $C_1$-$C_9$ alkoxyl group; a $C_1$-$C_9$ haloalkoxyl group; a $C_1$-$C_9$ thioalkyl group; a $C_1$-$C_9$ halothioalkyl group; a $C_3$-$C_9$ cycloalkyl group; a $C_2$-$C_{10}$ carboalkoxyl group; a cyano group; a phenyl group; a hydroxyl group;
R' represents an alkyl group, optionally selected from methyl, propyl, isopropyl; or the haloalkyl group trifluoromethyl; or hydrogen;
n is a number ranging from 0 to 2;
X represents an oxygen atom, a nitrogen or a sulfur atom; for the control of phytopathogens on vegetables or parts thereof.

The compounds having formula (I) can also be present in hydrated form by the coordination of any number of water molecules.

The compositions according to the present invention which comprise one or more salts of derivatives of salicylic acid (I) associated with at least one other fungicidal compound not corresponding to a salt of derivatives of salicylic acid having formula (I), are therefore advantageously characterized by inducing natural defense together with the direct effect of the cupric ion, forming an excellent control system of phytopathogens which exerts a synergic action with many active principles, representing an optimum instrument for anti-resistance strategies.

In particular, the fungicidal compound not corresponding to a salt of derivatives of salicylic acid having formula (I) can be selected from inhibitors of ergosterol biosynthesis, inhibitors of mitochondrial respiration, acylanilines, systemic anti-mildew fungicides, a dipeptide with a fungicidal activity, cytotropic anti-mildew fungicides, contact fungicides, cupric fungicides, inhibitor fungicides of melanin biosynthesis.

A fungicidal compound not corresponding to a salt of derivatives of salicylic acid having formula (I) is preferably selected from tetraconazole, difenoconazole, myclobutanil, flusilazole, epoxyconazole, fenpropimorf, fenpropidin, azoxystrobin, kresoxym methyl, trifloxystrobin, metalaxyl, benalaxyl in its racemic form or as an optically active R isomer (called IR 6141), iprovalicarb, ethaboxam, cyazofamid, cymoxanyl, mancozeb, clorotalonil, folpet, ditianon, copper hydroxide, copper oxychloride, cuprocalcium oxychloride.

For these preferred compositions, as can be observed in the experimental examples, an extremely important synergic effect has been identified.

In the above formulae, $C_1$-$C_9$ alkyl group refers to a linear or branched $C_1$-$C_9$ alkyl group, optionally substituted by one or more substituents, the same or different from each other.

Examples of this group are: methyl, ethyl, propyl, isopropyl, butyl, isobutyl, terbutyl.

$C_1$-$C_9$ haloalkyl group refers to a linear or branched alkyl group substituted by one or more halogen atoms, the same or different, optionally selected from fluorine, chlorine, bromine, iodine.

Examples of this group are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl.

$C_1$-$C_9$ alkoxyl group refers to a $C_1$-$C_9$ alkoxyl group, wherein the aliphatic portion is a $C_1$-$C_9$ alkyl group, as defined above.

Examples of this group are: methoxyl, ethoxyl.

$C_1$-$C_9$ haloalkoxyl group refers to a $C_1$-$C_9$ haloalkoxyl group, wherein the aliphatic portion is a $C_1$-$C_9$ haloalkyl group, as defined above.

Examples of this group are: trifluoromethoxyl, 1,1,2,2-tetrafluoroethyoxyl, 1,1,2,3,3,3-hexafluoropropyloxyl.

$C_1$-$C_9$ thioalkyl group refers to a $C_1$-$C_9$ thioalkyl group, wherein the aliphatic portion is a $C_1$-$C_9$ alkyl group, as defined above. Examples of this group are: thiomethyl, thioethyl.

$C_1$-$C_9$ halothioalkyl group refers to a $C_1$-$C_9$ halothioalkyl group, wherein the aliphatic portion is a $C_1$-$C_9$ haloalkyl group, as defined above.

Examples of this group are: trifluorothiomethoxyl, 1,1,2,2-tetrafluorothioethoxyl.

$C_3$-$C_9$ cycloalkyl group refers to a cycloalkyl group whose ring consists of 3-6 carbon atoms, optionally substituted by one or more substituents, the same or different to each other.

Examples of this group are: cyclopropyl, cyclobutyl, cyclopentyl, cyclohexyl.

$C_2$-$C_{10}$ carboalkoxyl group refers to a carboalkoxyl group, wherein the aliphatic portion is a $C_1$-$C_9$ alkyl group, as defined above.

Examples of this group are: carboxymethyl, carboxyethyl, carboxypropyl.

Optionally substituted refers to one or more substituents, the same or different, selected from the following groups: halogen atoms, alkyls, alkoxyls, alkylthio, cyano, hydroxy, aminocarbonyls, carboalkoxyls.

$R_2$ is preferably selected from fluorine, chlorine, methyl, trifluoromethyl, hydroxyl.

Some further examples of fungicides which can be used in the compositions according to the present invention are listed below. Among others, one or more of the following fungicides can therefore be selected:
1. as inhibitors of ergosterol biosynthesis, for example, triazole, imidazole, pyrimidine and pyridine fungicides and/or derivatives of morpholine or piperidine;
2. as inhibitors of mitochondrial respiration, for example, analogous synthetic products of strobilurine, or fenamidone, famoxadone, ethaboxam, fluazinam or cyazofamid;
3. among acylanilines, metalaxyl or benalaxyl, in their racemic form or as optically active R isomers, oxadixyl and/or ofurace;
4. as systemic anti-mildew fungicides, iprovalicarb, dimethomorph, flumetover, the Chinese product SYP-L-190, a dipeptide with a fungicidal activity, propamocarb and/or zoxamide;
5. as cytotropic anti-mildew fungicides, cymoxanyl;
6. as contact fungicides, chlorothalonil, folpet, thiram, propineb, maneb, zineb, dichlofluanide, tolilfluanide, captan, folpet and/or dithianon;
7. as cupric fungicide, copper hydroxide $Cu(OH)_2$, copper oxychloride ($3Cu(OH)_2.Cu(Cl)_2$), cuprocalcium oxychloride ($3Cu(OH)_2.Ca(Cl)_2$), and/or tribasic copper sulfate ($3Cu(OH)_2.Cu(SO_4)$);
8. as inhibitor fungicide of melanin biosynthesis, tricycloazole and/or carpropamid.

Examples of triazole fungicides are: tetraconazole, epoxyconazole, difenoconazole, etc.

Examples of pyrimidine fungicides are: nuarimol, fenarimil, etc.

Examples of derivatives of morpholine are: fenpropimorf, fenpropidin, spiroxamina.

Examples of analogous products of strobilurine are: azoxystrobin, kresoxim methyl, pyraclostrobin, etc.

Fungicidal compounds not corresponding to a salt of derivatives of salicylic acid having formula (I) are commercial compounds or products about to be commercialized. Their description can be easily fund in technical literature, for example in "The pesticide manual", 2000, XII edition, British Crop Protection Council Ed.

Dipeptide derivative with a fungicidal activity refers to one of the compounds among those claimed in patent application EP 1028125.

The compounds having formula (I) can be easily obtained by means of numerous synthetic methods. For illustrative but non-limiting purposes, for example, the following preparation for compounds having formula (I), wherein X has the meaning of oxygen and $R_1$ is a —CO—R' acyl group, is provided (Scheme A):

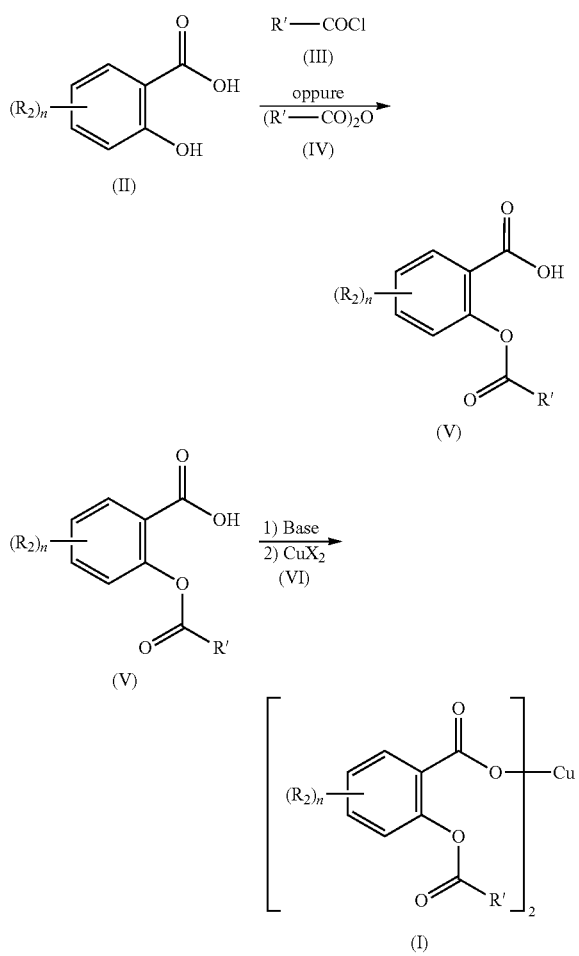

The acid having formula (II) is acylated with an acyl chloride having formula (III) in an organic solvent such as dichloromethane, or 1,2-dichloroethane, or ethyl acetate in the presence of an organic base, such as pyridine or triethylamine, or inorganic, such as sodium or potassium bicarbonate, or the acid having formula (II) is acylated with the anhydride (IV) under similar conditions, or also using the same anhydride (IV) as solvent. The acid derivative having formula (V) is then dissolved in water by means of an organic base, such as sodium or potassium bicarbonate, sodium or potassium hydroxide, and the copper salt (IV) is added to the resulting solution, wherein X can be a halogen, such as chlorine or bromine, or the sulfate ion, or perchlorate, dissolved in water, obtaining a compound having formula (I). Alternatively, it is possible to use copper hydroxide or carbonate in the presence of the acid form (V), with or without an additional base, such as an organic amine, for example triethylamine, as catalyst.

For the preparation of the compounds having formula (I), wherein X has the meaning of nitrogen and sulfur, the same procedure is adopted as described above, using the corresponding acids having formula (II).

The salts having formula (I) wherein $R_1$ has the meaning of hydrogen are analogously obtained from the compound (II) operating according to the procedure described for the transformation of the intermediate (V) into the salt (I).

The salts derivatives of salicylic acid having formula (I) alone or in compositions with at least one other active principle are capable of controlling many fungal and bacterial phytopathogens, also with a reduced sensitivity towards other fungicides.

For purely illustrative and without any limiting purposes, some examples are listed below, of phytopathogens controlled by compounds having formula (I) alone or in a mixture, together with examples of possible application crops:

*Plasmopara viticola* on grapes;
*Peronospora tabacina* on tobacco;
*Venturia inaequalis* on apple-trees;
*Bremia* on salads, spinach;
*Phytophthora* spp. on vegetables;
*Pseudoperonospora cubensis* on cucurbitaceae;
*Pyricularia orizae* on rice.

Both compositions containing one or more salts of derivatives of salicylic acid having formula (I), and salts of derivatives of salicylic acid having formula (I), object of the present invention, are capable of exerting a high fungicidal action of both a curative and preventive nature and additionally have a low or absence of phytotoxicity.

A further object of the present invention therefore relates to a method for controlling phytopathogen fungi in agricultural crops by the application of the compounds having formula (I) or mixtures of these associated with at least one other fungicidal compound not corresponding to a salt of derivatives of salicylic acid having formula (I).

More specifically, an object of the present invention relates to a method which can be applied to agricultural crops for controlling phytopathogens sensitive or tolerant to fungicides not corresponding to a salt of a derivative of salicylic acid having formula (I).

The quantity of compound to be applied for obtaining the desired effect can vary in relation to various factors such as, for example, the crop to be preserved, the type of pathogen, the degree of infection, the climatic conditions, the formulation adopted.

Doses of compound ranging from 10 g to 5 Kg per hectare generally provide sufficient control.

For practical use in agriculture, it is often convenient to adopt fungicidal compositions containing one or more compounds having general formula (I) or mixtures of these with at least one fungicidal compound not corresponding to a salt having formula (I).

The application of the compositions, object of the present invention, can take place on any part of the plant, for example on the leaves, stems, branches and roots or on the seeds themselves before sowing, or also on the ground in which the plant grows.

Compositions can be used, in the form of dry powders, wettable powders, emulsifiable concentrates, microemulsions, pastes, granulates, solutions, suspensions, etc.: the selection of the type of composition depends on the specific use.

The compositions are prepared according to the known methods, for example by diluting or dissolving the active substance with a solvent and/or solid diluent medium, optionally in the presence of surface-active agents.

Silica, kaolin, bentonite, talc, fossil flour, dolomite, calcium carbonate, magnesia, chalk, clays, synthetic silicates, attapulgite, sepiolite, can be used as solid inert diluents, or carriers.

In addition to water, various solvents such as aromatic solvents (xylols, mixtures of alkylbenzols); paraffins (petroleum fractions); alcohols (methanol, propanol, butanol, octanol, glycerin); amines; amides (N,N-dimethylformamide, N-methylpyrrolidone); ketones (cyclohexanone, acetone, acetophenone, isophorone, ethylamylketone); esters (isobutyl acetate, methyl esters of fatty acids obtained for example by the transesterification of vegetable oils), can be used as liquid diluents.

Sodium, calcium, triethanolamine salts, or triethylamine salts of alkylsulfonates, alkylarylsulfonates, or polyethoxylated alkylphenols, or fatty alcohols condensed with ethylene oxide, or polyoxyethylated fatty acids, or polyoxyethylated esters of sorbitol, or ligninsulfonates, can be used as surface-active agents.

The compositions can also contain special additives for particular purposes such as, for example, adhesion agents, such as gum arabic, polyvinyl alcohol, polyvinyl pyrrolidone, polyacrylates.

In the above compositions, the concentration of active substances varies from 0.1% to 98%, preferably from 0.5% to 90%.

If desired, it is possible to also add other compatible active principles to the compositions, object of the present invention, such as phytoregulators, antibiotics, herbicides, insecticides, fertilizers.

The following examples are provided for illustrative purposes only and do not limit the scope of the present invention.

EXAMPLE 1

Preparation of the Copper Salt of Acetylsalicylic Acid (Compound Nr. 1)

3 g of acetylsalicylic acid are added to a solution of 1.39 g of sodium bicarbonate in 15 cm$^3$ of water. When the acid is completely dissolved, a solution of 2.07 g of cupric sulfate in 15 cm$_3$ of water are slowly added dropwise. After 3 hours, the precipitate thus obtained is filtered and washed with hexane, obtaining, after drying in air, 3.4 g of compound Nr. 1 (yield: 48.4%). The analytical composition of compound Nr. 1 is indicated in Table 1.

EXAMPLE 2

The following; compounds, whose analytical composition is indicated in Table 1, were prepared analogously to the procedure described in Example 1:
copper salt of salicylic acid (Compound Nr. 2)
copper salt of 5-chlorosalicylic acid (Compound Nr. 3)
copper salt of 5-chloroacetylsalicylic acid (Compound Nr. 4)
copper salt of 5-hydroxysalicylic acid (Compound Nr. 5)
copper salt of 6-hydroxysalicylic acid (Compound Nr. 6)
copper salt of 3-methylsalicylic acid (Compound Nr. 7)
copper salt of 4-methoxysalicylic acid (Compound Nr. 8)

TABLE 1

| Compound | XR$_1$ | R$_2$ | % C [a,c] | % H [a,c] | % Cu [b,c] |
|---|---|---|---|---|---|
| 1 | OCOCH$_3$ | H | 49.41 (51.2) | 3.32 (3.28) | 16.04 (15.06) |
| 2 | OH | H | 46.72 (49.7) | 3.21 (2.96) | 19.23 (18.81) |
| 3 | OH | 5-Cl | 39.98 (41.31) | 2.45 (1.97) | 16.56 (15.63) |
| 4 | OCOCH$_3$ | 5-Cl | 42.09 (44.01) | 2.95 (2.44) | 13.51 (12.95) |
| 5 | OH | 5-OH | 42.87 (45.43) | 3.15 (2.70) | 19.46 (17.18) |
| 6 | OH | 6-OH | 43.67 (45.43) | 3.94 (2.70) | 18.62 (17.18) |
| 7 | OH | 3-CH$_3$ | 56.71 (57.59) | 3.98 (4.19) | 19.79 (19.04) |
| 8 | OH | 4-OCH$_3$ | 54.36 (52.55) | 4.02 (3.83) | 16.67 (17.38) |

Notes:
[a] values obtained by elemental analysis;
[b] values obtained by gravimetric analysis;
[c] the expected values are indicated in brackets.

EXAMPLE 3

Efficacy of Compound Nr. 1 Mixed with Another Fungicidal Compound in the Control of *Venturia inaequalis* on Apple-Tree in Preventive Leaf Application (Greenhouse Test) Table 2.

Leaves of wild-type apple-tree, cultivated in vases, in a conditioned environment (24±1° C., 70% relative humidity) are treated by spraying both sides of the leaves with compound Nr. 1 mixed with another fungicide dispersed in a hydroacetone solution at 20% by volume of acetone containing 0.3% of tween 20.

After remaining 48 hours in a conditioned environment, the plants are infected on the lower and higher sides with an aqueous suspension of spores of *Venturia inaequalis* (200, 000 spores per cm$^3$).

The plants are kept in a humidity saturated environment, at 21° C., for the incubation period of the fungus and, at the end of this period (14 days), the fungicidal activity is evaluated according to a percentage evaluation scale from 100 (healthy plant) to 0 (completely infected plant).

From the data indicated in Table 2, the synergic effect of the mixtures, consisting of compound Nr. 1 and another fungicide belonging to the various groups cited above, can be observed, compared with the efficacy calculated using the Limpel formula ("Pesticide Science" (1987), vol. 19, pages 309-315:

$$E = x + y - (xy/100)$$

wherein:
  E is the expected fungicidal activity, without synergic effects, from a mixture obtained by mixing g·x of the compound X with g·y of the compound Y;
  x is the activity of the compound X when used alone at a dose of g·x;
  y is the activity of the compound Y when used alone at a dose of g·y;
  When the fungicidal activity experimentally evaluated is greater than the value of E, this activity should be considered as a synergic effect.

TABLE 2

The preventive activity after a day on *Venturia inaequalis* of compound Nr. 1 at 125 ppm (g · x) is 95 (x)

| Fungicide | Dosage ppm (g · y) | Activity (y) | Activity of mixture according to Limpel (E) | Experimental mixture activity | Synergy factor |
|---|---|---|---|---|---|
| Tetraconazole | 60 | 38 | 96.9 | 100 | 1.03 |
| Difenoconazole | 100 | 36 | 96.8 | 97 | 1.00 |
| Myclobutanil | 200 | 35 | 96.75 | 98 | 1.01 |
| Flusilazole | 170 | 34 | 96.7 | 97 | 1.00 |
| Epoxyconazole | 80 | 30 | 96.5 | 97 | 1.00 |
| Fenpropimorf | 300 | 33 | 96.65 | 98 | 1.01 |
| Fenpropidin | 400 | 37 | 96.85 | 99 | 1.02 |
| Azoxystrobin | 0.11 | 35 | 96.75 | 98 | 1.01 |
| Kresoxym methyl | 0.45 | 35 | 96.75 | 98 | 1.01 |
| Trifloxystrobin | 1.8 | 40 | 97.0 | 100 | 1.03 |

EXAMPLE 4

Efficacy of Compound Nr. 1 Mixed with Another Fungicidal Compound in the Control of *Plasmopara viticola* on Grapes in Preventive Leaf Application (Greenhouse Test) Table 3.

Leaves of cultivar Dolcetto grape vines, cultivated in vases, in a conditioned environment (20±1° C., 70% relative humidity) are treated by spraying both sides of the leaves with compound Nr. 1 mixed with another fungicide dispersed in a hydroacetone solution at 10% by volume of acetone containing 0.3% of tween 20.

After remaining 24 hours in a conditioned environment, the plants are infected on the lower side with an aqueous suspension of spores of *Plasmopara viticola* (200,000 spores per cm³).

The plants are kept in a humidity saturated environment, at 21° C., for the incubation period of the fungus and, at the end of this period (7 days), the fungicidal activity is evaluated according to a percentage evaluation scale from 100 (healthy plant) to 0 (completely infected plant).

From the data indicated in Table 3, the synergic effect of the mixtures, consisting of compound Nr. 1 and another fungicide belonging to the various groups cited above, can be observed, compared with the efficacy calculated using the Limpel formula ("Pesticide Science" (1987), vol. 19, pages 309-315:

$$E = x + y - (xy/100)$$

wherein:
E is the expected fungicidal activity, without synergic effects, from a mixture obtained by mixing g·x of the compound X with g·y of the compound Y;
x is the activity of the compound X when used alone at a dose of g·x;
y is the activity of the compound Y when used alone at a dose of g·y;
When the fungicidal activity experimentally evaluated is greater than the value of E, this activity should be considered as a synergic effect.

TABLE 3

The preventive activity after a day on *Plasmopara viticola* of compound Nr. 1 at 30 ppm (g · x) is 53 (x)

| Fungicide | Dosage ppm (g · y) | Activity (y) | Activity of mixture according to Limpel (E) | Experimental mixture activity | Synergy factor |
|---|---|---|---|---|---|
| Metalaxyl | 0.05 | 34 | 68.98 | 77 | 1.12 |
| Metalaxyl * | 0.05 | 12 | 58.64 | 73 | 1.24 |
| Benalaxyl | 0.05 | 42 | 72.74 | 84 | 1.15 |
| IR 6141 | 0.025 | 40 | 71.8 | 86 | 1.20 |
| Iprovalicarb | 0.45 | 38 | 70.86 | 87 | 1.23 |
| Ethaboxam | 12 | 33 | 68.51 | 77 | 1.12 |
| IR 5885 | 0.22 | 39 | 71.33 | 87 | 1.22 |
| Cyazofamid | 4 | 31 | 67.57 | 76 | 1.12 |
| Cymozanyl | 7.5 | 34 | 68.98 | 74 | 1.03 |
| Mancozeb | 250 | 36 | 69.92 | 74 | 1.06 |
| Clorotalonil | 100 | 32 | 68.04 | 76 | 1.12 |
| Folpet | 50 | 30 | 67.1 | 77 | 1.15 |
| Dithianon | 37 | 37 | 70.39 | 83 | 1.18 |
| Copper hydroxide | 150 | 35 | 69.45 | 74 | 1.07 |
| Copper oxychloride | 200 | 34 | 68.98 | 73 | 1.06 |
| Cuprocalcium oxychloride | 250 | 36 | 69.92 | 76 | 1.09 |

* Test effected on an isolated portion of the phytopathogen with a reduced sensitivity.

EXAMPLE 5

Fungicidal Efficacy of Compounds Having Formula (I) in the Control of *Plasmopara viticola* on Grapes (Field Test) Table 4, Table 5 and Table 6.

The efficacy field tests for the control of *Plasmopara viticola* are carried out using an experimental scheme with randomized blocks which comprise 4 replications and 6-8 plants by repetition.

The grape plants, Barbera variety, are treated by spraying both sides of the leaves either with a compound having formula (I) or with a mixture containing one or more salts having formula (I) and another fungicide, object of the present invention, formulated as wettable powder WP50.

The tests are carried out by treatment at a fixed period of 7 days for the mixtures of a compound of formula (I) with IR6141 and at a fixed period of 10 days for the mixtures of a compound of formula (I) with IR 5885.

The measurements, made when the presence of the pathogen is observed on the non-treated blank plot, are effected on both the leaves and the cluster.

The measurement on the leaves is effected by counting 100 grape leaves per plot (total 400 leaves) and marking the leaf surface percentage struck by the disease.

The measurement on the clusters, on the other hand, is effected by analyzing all the clusters and considering the percentage of surface damaged.

The data relating to the field tests of compounds Nr. 2-4 compared with Mancozeb and copper oxychloride, are provided in Table 4.

TABLE 4

| Product | Dosage gpa/hl | Leaf disease % reduction | Cluster disease % reduction |
| --- | --- | --- | --- |
| Blank | | 100* | 98.86* |
| Compound nr. 2 | 128 | 89.47 | 91.52 |
| Compound nr. 3 | 150 | 90.40 | 92.00 |
| Compound nr. 4 | 50 | 90.10 | 90.80 |
| Copper Oxychloride | 800 | 82.00 | 87.02 |
| Mancozeb | 2000 | 88.50 | 88.50 |

(gpa/hl) = grams of active principle per hectoliter
*= incidence of the disease.

The data relating to the field tests of compounds Nr. 1-4, mixed with IR6141 are provided in Table 5, the data relating to the field tests of compounds Nr. 1, 2, 4 and 8, mixed with IR5885 are provided in Table 6.

TABLE 5

| Product | Dosage gpa/hl | Leaf disease % reduction | Cluster disease % reduction |
| --- | --- | --- | --- |
| Blank | | 99* | 95* |
| Compound nr. 1 + IR 6141 | 80 + 10 | 97 | 94 |
| Compound nr. 2 + IR 6141 | 80 + 10 | 96 | 94 |
| Compound nr. 3 + IR 6141 | 85 + 10 | 99 | 97 |
| Compound nr. 4 + IR 6141 | 40 + 10 | 95 | 95 |
| IR 6141 + Copper hydroxide | 10 + 110 | 93 | 90 |

(gpa/hl) = grams of active principle per hectoliter
*= incidence of the disease.

TABLE 6

| Product | Dosage gpa/hl | Leaf disease % reduction | Cluster disease % reduction |
| --- | --- | --- | --- |
| Blank | | 99* | 95* |
| Compound nr. 1 + IR 5885 | 100 + 12 | 99 | 98 |
| Compound nr. 2 + IR 5885 | 100 + 12 | 98 | 97 |
| Compound nr. 4 + IR 5885 | 40 + 12 | 99 | 98 |
| Compound nr. 8 + IR 5885 | 100 + 12 | 97 | 96 |

(gpa/hl) = grams of active principle per hectoliter
*= incidence of the disease.

The invention claimed is:

1. A composition containing one or more salts of derivatives of salicylic acid having formula (I):

$$\left[ (R_2)_n \underset{O}{\overset{X-R_1}{\diagdown}} O \right]_2 Cu \quad (I)$$

wherein:
R$_1$ represents a CO—R' acyl group;
R$_2$, the same or different when n is equal to 2, is a halogen selected from the group consisting of fluorine, chlorine, bromine and iodine; a C$_1$-C$_9$ alkyl group; a C$_1$-C$_9$ haloalkyl group; a C$_1$-C$_9$ alkoxyl group; a C$_1$-C$_9$ haloalkoxyl group; a C$_1$-C$_9$ thioalkyl group; a C$_1$-C$_9$ halothioalkyl group; a C$_1$-C$_9$ cycloalkyl group; a C$_2$-C$_{10}$ carboalkoxyl group; a cyano group;
or a hydroxyl group;
R' represents a hydrogen; a C$_1$-C$_9$ alkyl group; a C$_1$-C$_9$ haloalkyl group; a C$_1$-C$_9$ alkoxyl group; a C$_1$-C$_9$ haloalkoxyl group; a C$_2$-C$_{10}$ carboalkoxyl group; or a phenyl group;
n is a number ranging from 0 to 2;
X represents an oxygen atom;
in any molar ratio, with at least one fungicidal compound selected from the group consisting of tetraconazole, difenoconazole, myclobutanil, flusilazole, epoxiconazole, fenpropimorph, fenpropidin, azoxystrobin, kresoxim methyl, trifloxystrobin, metalaxyl, benalaxyl in its racemic form or as an optically active R isomer (called IR 6141), iprovalicarb, ethaboxam, cyazofamid, cymoxanil, mancozeb, chlorothalonil, folpet, dithianon, copper hydroxide, copper oxychloride, cuprocalcium oxychloride and IR5885.

2. The composition according to claim 1, characterized in that the compounds having formula (I) are present in hydrated form by the coordination of any number of water molecules.

3. The composition according to claim 1, characterized in that, in the compounds having formula (I), R$_2$ is selected from the group consisting of fluorine, chlorine, methyl, trifluoromethyl, and hydroxyl.

4. The composition according to claim 1, formulated as dry powders, wettable powders, emulsifiable concentrates, micro-emulsions, pastes, granulates, solutions, or suspensions.

5. The composition according to claim 1, further comprising adhesion agents selected from the group consisting of gum arabic, polyvinyl alcohol, polyvinylpyrrolidone, and polyacrylates, and/or other compatible active principles selected from the group consisting of phytoregulators, antibiotics, herbicides, insecticides and fertilizers.

6. The composition according to claim 1, characterized in that the concentration of the active substances ranges from 0.1% to 98% by weight.

7. The composition according to claim 1, characterized in that the concentration of the active substances ranges from 0.5% to 90% by weight.

8. A method for the control of phytopathogens on vegetables or parts thereof which comprises applying a fungicidal composition containing one or more salts of derivatives of salicylic acid having formula (I):

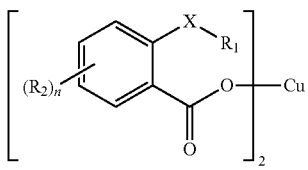

wherein:
- $R_1$ represents a CO—R' acyl group;
- $R_2$, the same or different when n is equal to 2, is a hydrogen, a halogen selected from the group consisting of fluorine, chlorine, bromine and iodine; a $C_1$-$C_9$ alkyl group; a $C_1$-$C_9$ haloalkyl group; a $C_1$-$C_9$ alkoxyl group; a $C_1$-$C_9$ haloalkoxyl group; a $C_1$-$C_9$ thioalkyl group; a $C_1$-$C_9$ halothioalkyl group; a $C_3$-$C_9$ cycloalkyl group; a $C_2$-$C_{10}$ carboalkoxyl group; a cyano group; a phenyl group; or a hydroxyl group;
- R' represents a hydrogen; a $C_1$-$C_9$ alkyl group; a $C_1$-$C_9$ haloalkyl group; a $C_1$-$C_9$ alkoxyl group; a $C_1$-$C_9$ haloalkoxyl group; a $C_1$-$C_{10}$ carboalkoxyl group; or a phenyl group;
- n is a number ranging from 0 to 2;
- X represents an oxygen atom;

in any molar ratio, with at least one fungicidal compound selected from the group consisting of tetraconazole, difenoconazole, myclobutanil, flusilazole, epoxiconazole, fenpropimorph, fenpropidin, azoxystrobin, kresoxim methyl, trifloxystrobin, metalaxyl, benalaxyl in its racemic form or as an optically active R isomer (called IR 6141), iprovalicarb, ethaboxam, cyazofamid, cymoxanil, mancozeb, chlorothalonil, folpet, dithianon, copper hydroxide, copper oxychloride, cuprocalcium oxychloride and IR5885.

9. A method for the control of phytopathogens on vegetables or parts thereof which comprises applying an effective amount of a composition of claim 1.

10. A method according to claim 8 wherein the phytopathogens are bacterial and fungal phytopathogens.

11. A method according to claim 8 where the phytopathogens are tolerant to a fungicidal compound not corresponding to a salt of derivatives of salicylic acid having formula (I).

12. A method according to claim 8 wherein the vegetables are genetically modified vegetable varieties.

13. A method according to claim 8 wherein the vegetables are genetically modified for amplifying the defense systems of the plants.

14. A method according to claim 8, wherein the vegetables are genetically modified vegetable varieties in which one or more genes expressing fungicidal proteins have been inserted, in response to variations in the content of the same salicylic acid in the tissues.

15. A method according to claim 8, wherein the phytopathogens controlled are *Plasmopara viticola* on grapes, *Peronospora tabacina* on tobacco, *Venturia inaequalis* on apple-trees, *Bremia* on salads, and spinach, *Phytophthora* spp. on vegetables, *Pseudoperonospora cubensis* on cucurbitacaea, and *Pyricularia orizae* on rice.

16. A method for fighting fungal infections consisting of applying a fungicidal composition according to claim 1, on plants, leaves, stems, branches and roots, or on the seeds themselves before sowing, or on the ground in which the plant grows.

* * * * *